United States Patent [19]

Nishihara et al.

[11] Patent Number: 5,278,212
[45] Date of Patent: Jan. 11, 1994

[54] FLOW MODIFIER FOR THERMOPLASTIC RESIN AND THERMOPLASTIC RESIN COMPOSITION CONTAINING THE SAME

[75] Inventors: Hajime Nishihara; Katsuaki Maeda; Hiroaki Ishikawa; Hiroshi Mikami, all of Kanagawa, Japan

[73] Assignee: Asahi Kasei Kogyo Kabushiki Kaisha, Osaka, Japan

[21] Appl. No.: 959,582

[22] Filed: Oct. 13, 1992

[30] Foreign Application Priority Data

Oct. 14, 1991 [JP] Japan .................. 3-264620

[51] Int. Cl.$^5$ .................. C08K 5/52; C08L 71/04
[52] U.S. Cl. .................. 524/141; 524/145; 558/162; 558/211; 252/400.2
[58] Field of Search .................. 558/162, 211; 524/141, 524/145; 252/400.2

[56] References Cited

U.S. PATENT DOCUMENTS

| | | | |
|---|---|---|---|
| 4,318,836 | 3/1982 | Abolins | 524/141 |
| 4,463,130 | 7/1984 | Serini et al. | 525/147 |
| 4,525,508 | 6/1985 | Lee, Jr. | 524/141 |
| 4,564,654 | 1/1986 | Serini et al. | 525/67 |
| 4,692,488 | 9/1987 | Kress et al. | 524/504 |
| 4,751,260 | 6/1988 | Kress et al. | 524/504 |

*Primary Examiner*—Kriellion S. Morgan
*Attorney, Agent, or Firm*—Armstrong, Westerman, Hattori, McLeland & Naughton

[57] ABSTRACT

A flow modifier for a thermoplastic resin, which is a hydroxyphenyl-containing organophosphorus compound represented by formula (I):

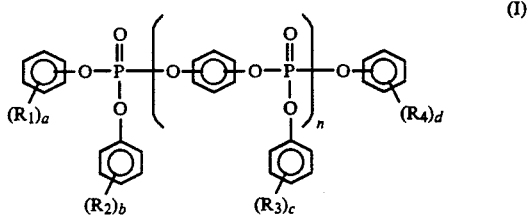

(I)

wherein $R_1$, $R_2$, $R_3$, and $R_4$ each represents a hydroxyl group,

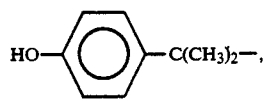

a hydrogen atom, or an alkyl group having 1 to 6 carbon atoms; a, b, c, and d each represents an integer of from 1 to 3; n represents 0 or an integer of from 1 to 3; when n is 0 or 1, the compound contains one hydroxyl group or

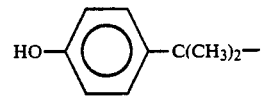

group per molecule; and when n is 2 or 3, the compound contains one or two, in total, of hydroxyl group and

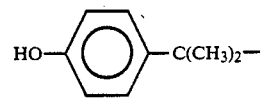

group per molecule and thermoplastic resin composition containing the flow modifier is disclosed.

10 Claims, 3 Drawing Sheets

FLOW MODIFIER FOR THERMOPLASTIC RESIN AND THERMOPLASTIC RESIN COMPOSITION CONTAINING THE SAME

FIELD OF THE INVENTION

This invention relates to a flow modifier for thermoplastic resins and a thermoplastic resin composition containing the same. More particularly, it relates to a specific organophosphorus compound which, when compounded with a thermoplastic resin if necessary together with a flame-retardant, endows the thermoplastic resin with excellent moldability and flame retardance.

BACKGROUND OF THE INVENTION

Thermoplastic resins have been steadily extending their use in various fields, such as automobile parts, appliances parts, and office automation equipment parts, because of their superior moldability and impact resistance as compared with inorganic materials, such as glass.

In these fields, in order to produce large-sized and thin-walled articles and to reduce the molding cycle, there has been an increasing demand for thermoplastic resins to have improved flow.

Various additives for improving flow of thermoplastic resins have been proposed to date. For example, addition of a mineral oil, which has been industrially adopted for a long time, improves flow but, in turn, causes a considerable reduction in heat resistance. It has been proposed to compound a thermoplastic resin with an ester of a polyhydric alcohol and a fatty acid (see JP-A-61-231045 and JP-A-61-275341 (the term "JP-A" as used herein means an "unexamined published Japanese patent application")); a higher fatty acid and a metal salt thereof (see JP-A-62-132951); a higher fatty acid metal salt and a specific phosphorous ester (see JP-A-62-190242); a fatty acid amide or an aliphatic alcohol and ethylene-bis-stearamide (see JP-A-62-257951); an ester of a higher fatty acid and a higher alcohol (e.g., stearyl stearate) (see JP-A-2-135219); or an isocyanuric ester compound (see JP-A-2-194047). Some making only insufficient improvement in flow, or some seriously impairing the heat resistance of the resin, and none of them provides a satisfactory thermoplastic resin composition.

On the other hand, aromatic phosphoric esters, such as triphenyl phosphate and tricresyl phosphate, are known to be effective to improve flow of thermoplastic resins. However, they not only bring about a marked reduction in heat resistance but generate decomposition gases on injection molding. The decomposition gases are condensed and deposited on the wall of an injection mold, so-called "mold deposit" resulting in impairment of the appearance of the resulting molded articles.

For example, a resin composition comprising a vinyl aromatic resin, polyphenylene ether, an aromatic phosphoric ester, and a nitrogen-containing compound is disclosed in JP-A- 54-38348, JP-A-54-38349, and EP 311909. Mainly comprising polyphenylene ether of low flowability, the resin composition has poor moldability. Besides, use of the aromatic phosphoric ester (e.g., triphenyl phosphate) causes mold deposit and reduction in heat resistance.

A combination of a hydroxyl-containing aromatic phosphoric ester and a phenol resin is disclosed in JP-A-1-223158, but the publication gives no reference to a combination of the additive with a thermoplastic resin, still less expectation of improving flow of a thermoplastic resin while retaining heat resistance, impact resistance, and flame retardance.

Further, a polyester resin composition containing tris(hydroxyphenyl) phosphate is disclosed in JP-A-50-98956. However, since the organophosphorus compound used contains three hydroxyl groups per molecule, it has poor compatibility with polyester only to provide a resin composition having imbalance of heat resistance, flow, and impact resistance.

SUMMARY OF THE INVENTION

An object of the present invention is to provide a flow modifier for a thermoplastic resin having small influence on impact resistance and heat resistance.

Another object of the present invention is to provide a thermoplastic resin composition having excellent moldability.

A further object of the present invention is to provide a thermoplastic resin composition excellent in moldability and flame retardance.

The inventors have studied to develop a flow modifier for thermoplastic resins which improves flow while minimizing reductions in impact resistance and heat resistance and causing no mold deposit. As a result, it has now been found that the above objects of the present invention are accomplished by using a specific organophosphorus compound.

The present invention relates to a flow modifier for a thermoplastic resin comprising a hydroxyphenyl-containing organophosphorus compound represented by formula (I):

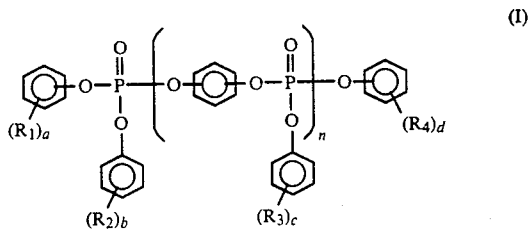

wherein $R_1$, $R_2$, $R_3$, and $R_4$ each represents a hydroxyl group,

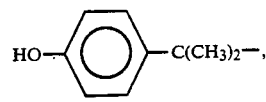

a hydrogen atom, or an alkyl group having 1 to 6 carbon atoms; a, b, c, and d each represents an integer of from 1 to 3; n represents 0 or an integer of from 1 to 3; when n is 0 or 1, the compound contains one hydroxyl group or

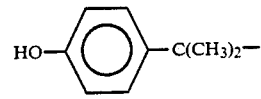

group per molecule; and when n is 2 or 3, the compound contains one or two, in total, of the hydroxyl group and

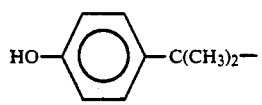

group per molecule.

The present invention also relates to a thermoplastic resin composition containing the hydroxyphenyl-containing organophosphorus compound represented by formula (I) as a flow modifier.

The present invention further relates to a thermoplastic resin composition containing the hydroxyphenyl-containing organophosphorus compound represented by formula (I) as a flow modifier and at least one flame-retardant selected from the group consisting of red phosphorus and a triazine skeleton-containing compound.

DETAILED DESCRIPTION OF THE INVENTION

Figure 1:
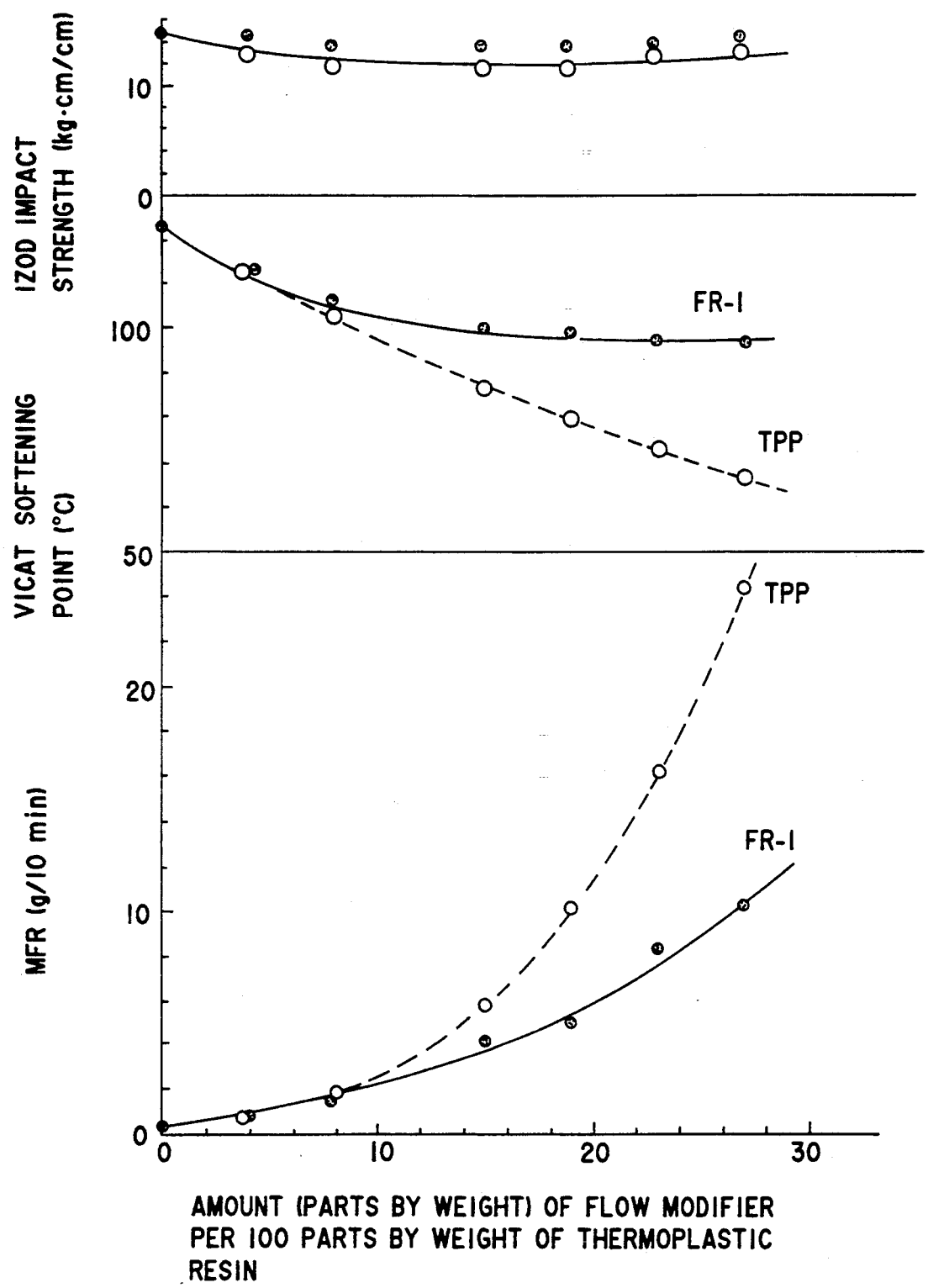
FIG. 1 is a graph showing the relationship of the amount (parts by weight) of a hydroxyphenyl-containing organophosphorus compound (FR-1) or an organophosphorus compound containing no hydroxyphenyl group (TPP) per 100 parts by weight of a thermoplastic resin used in Examples 1 to 5 and Comparative Examples 1 to 6 to Izod impact strength, Vicat softening point, or melt flow rate (MFR) of a resin composition containing the same.

The flow modifier according to the present invention mainly comprises a specific organophosphorus compound represented by formula (I). A thermoplastic resin composition obtained by compounding the flow modifier of the present invention with a thermoplastic resin has surprising advantages as hereinafter described in detail.

The thermoplastic resin composition according to the present invention comprises (A) a thermoplastic resin, (B) a flow modifier of the present invention, and, if desired, (C) at least one flame-retardant selected from red phosphorus and a triazine skeleton-containing compound.

Component (A) forms a major proportion of the molding resin composition, serving for maintenance of strength of molded articles. Component (B) is for improvement of flow while retaining heat resistance and impact resistance inherent to the thermoplastic resin. Component (C) is for endowing component (A) with flame retardance in cooperation with component (B).

As a result of our study, it has been revealed that a remarkable improvement of flow can be obtained while retaining heat resistance and impact resistance of component (A) when components (A) and (B) are combined with a specific difference in polarity therebetween. The "polarity" as referred to herein can be quantitatively expressed in terms of a solubility parameter (hereinafter abbreviated as SP value). If the difference in polarity between components (A) and (B) is too large, compatibility therebetween would be reduced, resulting in phase separation. With the polarity of component (B) being very close to that of component (A), although component (B) is completely mixed to exert a remarkable plasticizing effect to improve flow, the heat resistance of the resulting composition would be greatly reduced, and the entanglement of high-molecular chains would be eliminated, resulting in reduction of impact resistance. Accordingly, component (B) should be so selected as to have a proper polarity difference from component (A), with which partial compatibilization is attained, and the excellent effects of component (B) can be fully enjoyed. A preferred difference in SP value is from 0.5 to 2.0 $(cal/cm^3)^{\frac{1}{2}}$.

Thermoplastic resins which can be used as component (A) include polystyrene resins, polyolefin resins, polyvinyl chloride resins, polyphenylene ether resins (hereinafter abbreviated as PPE), polyamide resins, polyphenylene sulfide resins, polycarbonate resins, and polymethacrylate resins, and mixtures of two or more thereof; with polystyrene resins, PPE, and polycarbonate resins being preferred. The polystyrene resins may be rubber-modified or unmodified styrene resins. The most preferred of these thermoplastic resins is a polymer blend of a rubber-modified styrene resin and PPE.

The rubber-modified styrene resin is a polymer comprising a vinyl aromatic polymer matrix having dispersed therein rubbery polymer particles, which can be prepared by reacting a graft-polymerizable monomer mixture comprising an aromatic vinyl monomer and, if desired, a copolymerizable vinyl monomer in the presence of a rubbery polymer by known techniques, such as bulk polymerization, bulk suspension polymerization, solution polymerization, or emulsion polymerization.

Specific examples of such rubber-modified styrene resins are impact-resistant polystyrene (HIPS), an acrylonitrile-butadiene-styrene copolymer (ABS resin), an acrylonitrile-acrylic rubber-styrene copolymer (AAS resin), and an acrylonitrile-ethylenepropylene rubber-styrene copolymer (AES resin).

The rubbery polymer to be used for producing the rubber-modified styrene resins must have a glass transition temperature (Tg) of not higher than $-30°$ C. If the Tg exceeds $-30°$ C., the impact resistance would be reduced.

Specific examples of suitable rubbery polymers include diene rubbers, such as polybutadiene, poly(styrenebutadiene), and poly(acrylonitrile-butadiene); saturated rubbers obtained by hydrogenation of the above diene rubbers; acrylic rubbers, such as isoprene rubber, chloroprene rubber, and polybutyl acrylate; and an ethylene-propylene-diene terpolymer (EPDM), with the diene rubbers being particularly preferred.

The aromatic vinyl monomer, an essential component of the graft-polymerized monomer mixture, includes styrene, α-methylstyrene, p-methylstyrene, p-chlorostyrene, p-bromostyrene, and 2,4,5-tribromostyrene, with styrene being the most preferred. Styrene may be combined with a minor proportion of other aromatic vinyl monomers. The monomer mixture preferably contains at least 60% by weight of the aromatic vinyl monomer.

The graft-polymerizable monomer mixture may contain one or more of other monomers copolymerizable with the above-described aromatic vinyl monomer. For example, an unsaturated nitrile monomer, e.g., acrylonitrile or methacrylonitrile, may be used for the purpose of increasing oil resistance. The monomer mixture may also contain an acrylic ester monomer having an alkyl group of 1 to 8 carbon atoms for the purpose of decreasing the melt viscosity at the time of polymer blending. The monomer mixture may furthermore contain α-methylstyrene, acrylic acid, methacrylic acid, maleic anhydride, an N-substituted maleimide, etc. for the purpose of further improving heat resistance. The proportion of the vinyl monomers copolymerizable with the above-described vinyl aromatic monomer in the monomer mixture is preferably less than 40% by weight.

The rubber-modified styrene resin preferably comprises from 5 to 80% by weight, and more preferably from 10 to 50% by weight, of the rubbery polymer and from 20 to 95% by weight, and more preferably from 50 to 90% by weight, of the graft-polymerizable monomer mixture. Otherwise, the resulting resin composition tends to lose the balance between impact resistance and rigidity. The rubber polymer particles in the rubber-modified styrene resin preferably have a particle diameter of from 0.1 to 5.0 μm, and particularly from 0.2 to 3.0 μm. Out of this range, the impact resistance tends to be deteriorated.

As a measure of molecular weight, the rubber-modified styrene resin preferably has a reduced viscosity ($\eta_{sp/c}$) ranging from 0.30 to 0.80 dl/g, and particularly from 0.40 to 0.60 dl/g, as measured in a 0.5 g/dl toluene solution at 30° C. Molecular weight adjustment in the above-recited reduced viscosity range may be carried out by controlling the amount of a polymerization initiator, the polymerization temperature, the amount of a chain transfer agent, and the like. For example, the reduced viscosity can be increased by reducing the amounts of a polymerization initiator and a chain transfer agent, or lowering the polymerization temperature.

PPE as component (A) is preferably a homo- and/or copolymer comprising a repeating unit represented by formula (II):

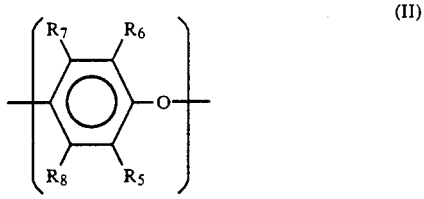

(II)

wherein $R_5$, $R_6$, $R_7$, and $R_8$, which may be the same or different, each represents a hydrogen atom or a substituted or unsubstituted hydrocarbon group.

PPE comprising the repeating unit (II) preferably includes poly(2,6-dimethyl-1,4-phenylene ether) and a copolymer of 2,6-dimethylphenol and 2,3,6-trimethylphenol, with the former being particularly preferred. The process for producing PPE is not particularly restricted. For example, PPE can easily be obtained by oxidative polymerization of, e.g., 2,6-xylenol in the presence of a cuprous salt-amine complex as a catalyst as described in U.S. Pat. No. 3,306,874. The processes disclosed in U.S. Pat. Nos. 3,306,875, 3,257,357, and 3,257,358, JP-B-52-17880 (the term "JP-B" as used herein means an "examined published Japanese patent application"), and JP-A-50-51197 may also be adopted.

PPE preferably has a reduced viscosity ($\eta_{sp/c}$) ranging from 0.20 to 0.7 dl/g, and particularly from 0.30 to 0.60 dl/g, as measured in a 0.5 g/dl chloroform solution at 30° C. Adjustment of the reduced viscosity can be effected by, for example, controlling the amount of the catalyst to be used in the above-mentioned process.

Polycarbonate resins as component (A) include 4,4'-dioxodiarylalkane polycarbonates, such as 2,2'-(4,4'-dihydroxydiphenyl)propane carbonate.

The organophosphorus compound represented by formula (I) which can be used as a main component of the flow modifier (component (B)) contains one- or two hydroxyphenyl groups per molecule. Should it contain three or more hydroxyphenyl groups, it would have too high polarity (too a high SP value) relative to component (A), resulting in phase separation due to poor compatibility. Those containing no hydroxyphenyl group have very good compatibility with a thermoplastic resin to exhibit a high plasticizing effect but cause serious reduction in heat resistance. Accordingly, the compound of formula (I) must contain one hydroxyphenyl group when n is 0 or 1 or one or two hydroxyphenyl groups when n is 2 or 3. The flow can be improved by virtue of moderate compatibility of the compound without adversely affecting heat resistance and impact resistance.

The organophosphorus compound of formula (I) can be prepared by a condensation reaction of phosphorus oxychloride, an aromatic hydroxyl compound, and an aromatic dihydroxy compound in the presence of aluminum chloride as a catalyst. The details of the preparation are described, e.g., in JP-A-1-223158.

Specific examples of the organophosphorus compound of formula (I) are (3-hydroxyphenyl)diphenyl phosphate, di(3-hydroxyphenyl)phenyl phosphate, 1,3-phenylenebis(3-hydroxyphenyl)phenyl phosphate, 1,3-phenylenediphenyl phosphate, (3-hydroxyphenyl)phenyl phosphate, (3-hydroxyphenyl)dicresyl phosphate, di(3-hydroxyphenyl)cresyl phosphate, 1,3-phenylenebis(3-hydroxyphenyl)cresyl phosphate, 1,3-phenylenedicresyl phosphate, (3-hydroxyphenyl)cresyl phosphate, (3-hydroxyphenyl)-di-2,6-xylyl phosphate, di(3-hydroxyphenyl)-2,6-xylyl phosphate, 1,3-phenylenebis(3-hydroxyphenyl)-2,6-xylyl phosphate, 1,3-phenylene-di-2,6-xylyl phosphate, (3-hydroxyphenyl)-2,6-xylyl phosphate, and mixtures of two or more thereof.

Of these, organophosphorus compounds represented by formula (III) are preferably used in the present invention:

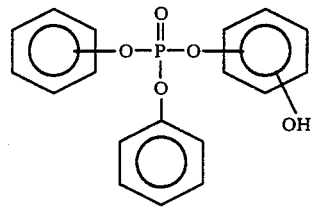

wherein the hydroxy group is at the meta- or para-position.

The flow modifier obtained by the above-mentioned condensation reaction may contain an organophosphorus compound containing hydroxyl-containing substituents more than the number as specified in the definition of formula (I). This being the case, however, it is preferable that the flow modifier should contain the specific hydroxyphenyl-containing organophosphorus compound of formula (I) in a proportion of at least 20% by weight.

If desired or unavoidabily, the resin composition of the present invention may further contain organophosphorus compounds other than the compound of formula (I) as far as the proportion of the compound of formula (I) in the total organophosphorus compounds is 20% by weight or more. As long as the proportion of the organophosphorus compounds other than the compound (I) in the total organophosphorus compounds is so controlled, it is possible to render a thermoplastic resin flame retardant without being accompanied by disadvantages associated with the conventional flame retardation techniques, such as reduction in impact resistance, reduction in heat resistance, or deterioration of an appearance of a molded article due to mold deposit.

Specific examples of other organophosphorus compounds which may be used in the present invention are triphenyl phosphate, tritolyl phosphate, trixylyl phosphate, tris(2-ethylhexyl) phosphate, tris(nonylphenyl) phosphate, tricresyl phosphate, 1,3-phenylenebisdiphenyl phosphate, triphenylphosphine, triphenylphosphine oxide, tritolylphosphine oxide, trinonylphenylphosphine oxide, tris(n-butyl)phosphine oxide, and benzylbisphenylphosphine oxide, and mixtures of two or more thereof.

In order to endow the resin composition of the present invention with further improved flame retardance, the composition may further contain (C) a flame-retardant selected from the group consisting of red phosphorus and a triazine skeleton-containing compound.

Red phosphorus includes not only general red phosphorus but surface-treated red phosphorus. The surface-treated red phosphorus includes red phosphorus coated with a film of a metal hydroxide, such as aluminum hydroxide, magnesium hydroxide, zinc hydroxide, or titanium hydroxide; red phosphorus coated with a film comprising such a metal hydroxide and a thermosetting resin; red phosphorus having thereon such a metal hydroxide coat and further having thereon a thermosetting resin coat; and electroless plated red phosphorus.

Where it is necessary to appreciably suppress generation of phosphine during kneading and extrusion of the resin composition, it is recommended to use (i) electroless plated red phosphorus and/or (ii) an electroless plated red phosphorus/hydrated metal compound mixture encapsulated in a thermoplastic resin.

The electroless plated red phosphorus (i) can be prepared by treating the surface of red phosphorus particles with a reducing catalyst and suspending the particles in water to carry out a reaction with a metal salt and a phosphoric acid type reducing agent in the presence of a complexing agent. The red phosphorus particles preferably have a particle size of 5 to 50 μm.

Metals for the electroless plating films formed on the red phosphorus particles are not particlularly limited, and they are preferably selected from Fe, Ni, Co, Cu, Zn, Mn and an alloy thereof, with Ni or a Ni alloy being particularly preferred. A preferred thickness of the plating film varies depending on the kind of metal used and it should be within the rage that the plating film can retain sufficient durability. A electroless plating film of 5 to 10 μm in thickness suffices to completely prevent generation of phosphine gas.

The encapsulated red phsphorus based mixture (ii) can be prepared by dissolving a thermoplastic resin in a water-soluble organic solvent to which the electroless plated red phosphorus and a hydrated metal compound are then uniformly dispersed, pouring the dispersion into water as a solidifying medium to granulate, and drying the resulting granules.

Examples of the hydrated metal compound include cerium hydroxide, aluminuum hydroxide, magnesium hydroxide and tin hydroxide. The hydrated metal compound is preferably small in particle size so as to ensure uniform dispersion of the compound in the resin capsules, and the particle size is preferably 5 to 10 μm and more preferably 3 to 5 μm. The hydrated metal compound is preferably contained in an amount of 50 to 150 parts by weight per 100 parts by weight of the electroless plated red phosphorus.

The triazine skeleton-containing compound as component (C) acts as a flame retardation assistant for the phosphorus-containing compound. Specific examples of such a compound include melamine cyanurate of formula (1), melamine phosphate of formula (2), melam of formula (3), melem of formula (4), mellon (a product obtained by deammonium reaction of three moles of melem at 600° C. or higher, generating three moles of ammonia), succinoguanamine of formula (5), melamine resins having the structure of formula (6), BT resins having the structure of formula (7), melamine, adipoguanamine and methylglutaroguanamine.

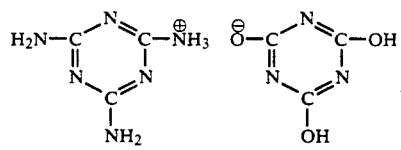

(1)

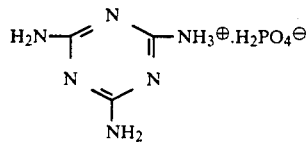

(2)

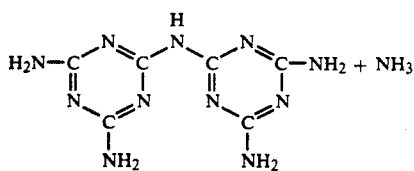
(3)

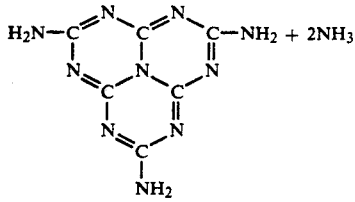
(4)

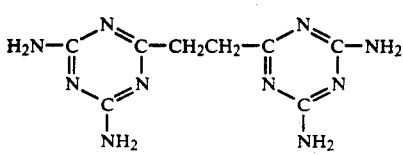
(5)

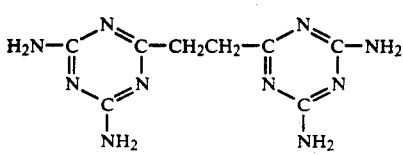
(6)

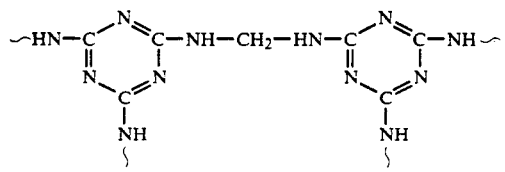

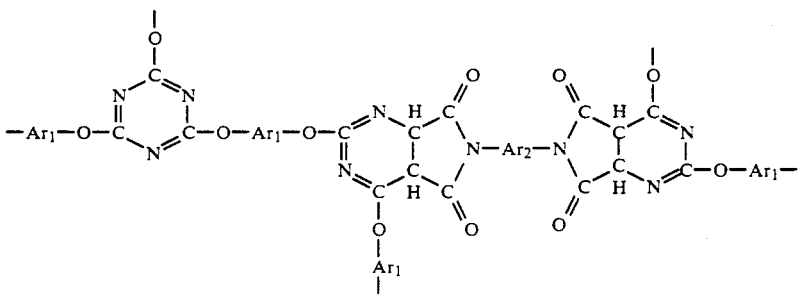
(7)

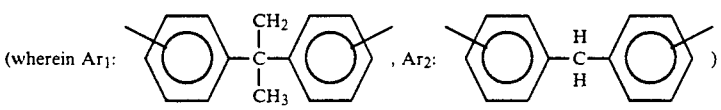

The proportions of components (B) and (C) in the resin composition are preferably from 5 to 50 parts by weight, particularly from 10 to 30 parts by weight, and up to 30 parts by weight, particularly from 5 to 20 parts by weight, respectively, per 100 parts by weight of component (A). Within these ranges, excellent balance among moldability (flow), heat resistance, impact resistance, and flame retardance can be maintained.

The resin composition of the present invention is prepared by, for example, melt-kneading the above-mentioned components in a single-screw extruder, a twin-screw extruder, etc. If desired, various additives may be compounded at the time of melt-kneading. Examples of useful additives are antioxidants, e.g., hindered phenol; ultraviolet absorbents, e.g., benzotriazole and hindered amine; tin based heat stabilizers; other inorganic or halogen-containing flame-retardants; lubricants, e.g., stearic acid and zinc stearate; fillers; reinforcements, e.g., glass fiber; and colorants, such as dyes and pigments.

In case fluidity of the resin composition is needed to be increased, higher fatty acid amides may further be compounded therein. The higher fatty acid amide is a reaction product of a diamine or aminoalcohol with a higher fatty acid preferably having an alkyl or alkenyl group of 11 to 21 carbon atoms, particularly preferably stearic acid. The diamine and aminoalcohol are preferably those of hydrocarbons having 2 to 10 carbon atoms, exemplified with ethylenediamine, monoethanolamine, 3-amino-1-propenol and 4-amino-1-butanol. Ethylenebisstearamide is particularly preferred as the higher fatty acid amide since the compound effectively improves the fluidity of the resin composition without any deterioration in falme retardance, heat resistance and impact resistance.

The thermoplastic resin composition according to the present invention can be molded with easy flow by injection molding or extrusion to provide molded articles excellent in flame retardance, heat resistance, and impact resistance.

The present invention is now illustrated in greater detail with reference to Examples, but it should be understood that the present invention is not construed as being limited thereto. All the parts, percents, and ratios are by weight unless otherwise indicated.

Various measurements in Examples and Comparative Examples were made as follows.

1) WEIGHT-AVERAGE PARTICLE SIZE OF RUBBERY POLYMER

A photomicrograph was taken of a section of a resin composition with a transmission electron microscope. The diameter of the rubbery polymer particles of a rubber-modified styrene resin was measured. A weight-average particle size can be obtained from $\Sigma Ni \cdot Di^4 / \Sigma Ni \cdot Di^3$, wherein Ni is the number of rubbery polymer particles having a diameter Di.

2) REDUCED VISCOSITY ($\eta_{sp/c}$)

To 1 g of a rubber-modified styrene resin were added 18 ml of methyl ethyl ketone and 2 ml of methanol. The mixture was shaken at 25° C. for 2 hours followed by centrifugation at 5° C. and 18000 rpm for 30 minutes. The supernatant liquor was separated, and the resinous content was precipitated in methanol and dried.

In toluene was dissolved 0.1 g of the thus recovered resinous content to a concentration of 0.5 g/dl. A 10 ml aliquot of the toluene solution was placed in a Ostwald-Fenske viscometer, and the flowing time ($t_1$) of the solution at 30° C. was measured. Separately, the flowing time ($t_0$) of toluene alone was measured in the same manner. The reduced viscosity ($\eta_{sp/c}$) of the rubber-modified styrene resin was calculated by equation:

$$\eta_{sp/c} = \frac{t_1/t_0 - 1}{c} \times c$$

wherein c is a polymer concentration (g/dl).

The reduced viscosity ($\eta_{sp/c}$) of PPE (component A) was also measured in the same manner, except that 0.1 g of the recovered resinous content was dissolved in chloroform to a concentration of 0.5 g/dl.

3) IZOD IMPACT STRENGTH

Measured on a V-notched, $\frac{1}{8}$ inch-thick specimen in accordance with ASTM-D256 at 23° C.

4) VICAT SOFTENING POINT

Measured in accordance with ASTM-D1525. Taken as a measure of heat resistance.

5) MELT FLOW RATE (MFR)

Measured in accordance with ASTM-D1238. Taken as a measure of flow. Calculated from an extrusion rate per 10 minutes (g/10 min) measured at a temperature of 200° C. under a load of 5 kg.

6) FLAME RETARDANCE AND NON-DRIPPING PROPERTIES

Evaluated by a vertical burning (VB) test in accordance with UL-94. A $\frac{1}{8}$ inch-thick specimen was used.

7) PHOSPHINE DETERMINATION

A funnel was put right above the vent port of an extruder or right above the specimen under burning test, and 10 ml of the exhaust gas was collected through a filter and introduced into a column of a gas chromatograph by means of an automatic sampler. Gas chromatography was conducted using a column "CHROMATOTEC GGC-01" (manufactured by GA-STEC), a controlled potential electrolysis type gas detector "PED", and a filler "Porapak QS".

Materials used in Examples and Comparative Examples were prepared as follows.

1) THERMOPLASTIC RESIN

1-1) Rubber-Modified Styrene Resin (HIPS-1)

Polybutadiene (cis-1,4 bond/trans-1,4 bond/vinyl-1,2 bond=95/2/3) was dissolved in a mixed solvent to prepare a uniform solution consisting of:

| | |
|---|---|
| Polybutadiene | 10.5% |
| Styrene | 72.2% |
| Ethylbenzene | 15.0% |
| Mineral oil | 2.0% |
| α-methylstyrene dimer | 0.27% |
| 1,1-Bis(t-butylperoxy)-3,3,5-trimethylcyclohexane | 0.03% |

The solution was forwarded continuously to a four-staged reactor equipped with a stirrer in each stage, and polymerization was conducted at 126° C. and 190 rpm in the first stage, 133° C. and 50 rpm in the second stage, 140° C. and 20 rpm in the third stage, and 155° C. and 20 rpm in the fourth stage. Subsequently, the polymerization mixture (solid content: 73%) was introduced into a devolatizing apparatus to remove the unreacted monomers and the solvent. The resulting rubber-modified styrene resin (designated as HIPS-1) was found to have a rubber content of 14%, a rubber weight-average particle size of 2.4 μm, and a reduced viscosity $\eta^{sp/c}$ of 0.53 dl/g.

1-2) Rubber-Modified Styrene Resin (HIPS-2)

Commercially available HIPS having the following composition (reduced viscosity $\eta_{sp/c}$: 0.79 rubber weight-average particle size: 1.25 μm) was used.

| | |
|---|---|
| Polybutadiene (cis-1,4 bond/trans-1,4 bond/vinyl-1,2 bond = 95/2/3) | 12.3% |
| Polystyrene | 87.53% |
| Mineral oil | 0.17% |

1-3) Rubber-Modified Styrene Resin (HIPS-3)

HIPS-3 was prepared in the same manner as for HIPS-1, except for using 2% of styrene in place of the mineral oil. HIPS-3 had a rubber content of 14%, a rubber weight-average particle size of 2.4 μm, and a reduced viscosity $\eta_{sp/c}$ of 0.53 dl/g.

1-4) PPE

A stainless steel-made reactor equipped with an oxygen inlet at the bottom thereof and a cooling coil and a stirring blade in the inside thereof was thoroughly purged with nitrogen. A solution of 8.75 kg of 2,6-xylenol, 54.8 g of cupric bromide, and 1110 g of di-n-butylamine in a mixed solvent of 20 l of toluene, 16 l of n-butanol, and 4 l of methanol was charged in the reactor and allowed to polymerize at an inner temperature of 30° C. for 180 minutes with stirring while bubbling with oxygen. After completion of the polymerization, the polymer precipitated was collected by filtration. To the polymer was added a mixture of methanol and hydrochloric acid to decompose any residual catalyst, and the polymer was thoroughly washed with methanol and dried to obtain a PPE powder. The reduced viscosity of PPE was 0.55 dl/g.

PPE was mixed with polystyrene, "Asahi Kasei Polystyrene 685" produced by Asahi Chemical Industry Co., Ltd., at a ratio of the former to the latter of 70/30, and the polymer blend was melt-kneaded in a twin-screw extruder at 350° C. and pelletized. The resulting pellet was designated PPE-MB.

1-5) ABS

A commercially available acrylonitrile-butadienestyrene copolymer (26/14/60) produced by Asahi Chemical Industry Co., Ltd. was used.

1-6) Polycarbonate (PC)

A commercially available polycarbonate resin, "Novarex 7025 A" produced by Mitsubishi Kasei Corporation, (hereinafter abbreviated as PC) was used.

2) FLOW MODIFIER

2-1) Hydroxyphenyl-Containing Organophosphorus Compound (FR-1)

In a flask were charged 122.7 parts of phenol and 0.87 part of aluminum chloride, and 100 parts of phosphorus oxychloride was added thereto dropwise at 90° C. over 1 hour (phenol:aluminum chloride:phosphorus oxychloride molar ratio =2.0:0.01:1.0). To the intermediate product (A) thus formed was added 71.7 parts (molar ratio: 1.0) of resorcin to further continue a reaction. During the reaction, the temperature was gradually elevated to a final temperature of 180° C. to complete esterification. The reaction product was cooled and washed with water. The catalyst and the chlorine content were removed to obtain a phosphoric ester mixture (designated FR-1). As a result of gel-permeation chromatography (GPC), the mixture was found to comprise diphenyl resorcinyl phosphate of formula (a) shown below (hereinafter referred to as TPP-OH), triphenyl phosphate (hereinafter abbreviated as TPP), and an aromatic condensed phosphoric ester of formula (b) shown below (hereinafter referred to as TPP dimer) at a ratio of 54.2/18.3/27.5.

TPP—OH:

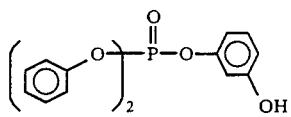

(a)

TPP Dimer:

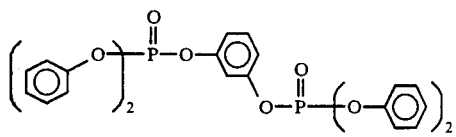

(b)

2-2) Hydroxyphenyl-Containing Organophosphorus Compound (FR-2)

FR-2 was prepared in the same manner as for FR-1, except for replacing resorcin with hydroquinone. The GPC analysis revealed that FR-2 comprises diphenyl hydroquinonyl phosphate of formula (c) shown below (hereinafter referred to as TPP-OH-P), TPP, an aromatic condensed phosphoric ester of formula (d) shown below, wherein n=1 (i.e., TPP dimer), and an aromatic condensed phosphoric ester of formula (d) wherein n≧2 (hereinafter referred to as TPP oligomer) at a ratio of 64.6/12.4/17.0/6.0.

TPP—OH—P:

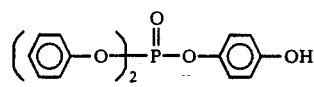

(c)

TPP Dimer and TPP Oligomer:

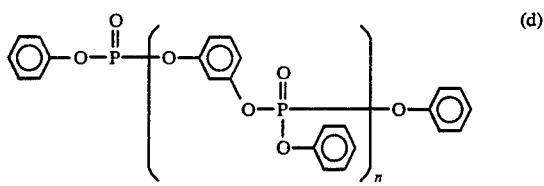

(d)

n = 1 TPP dimer
n ≧ 2 TPP oligomer

2-3) Hydroxyphenyl-Containing Organophosphorus Compound (FR-3)

FR-3 was prepared from the same starting materials as used for FR-1 but at varied molar ratio as follows.

In a flask were charged 61.4 parts of phenol and 0.87 part of aluminum chloride, and 100 parts of phosphorus oxychloride was added thereto dropwise at 90° C. over 1 hour (phenol:aluminum chloride:phosphorus oxychloride molar ratio: 1.0:0.01:1.0). To the intermediate product (B) was added 143.4 parts (molar ratio: 2.0) of resorcin to conduct a reaction. The resulting intermediate product (C) was further reacted with the intermediate product (A) obtained in the preparation of FR-1 at an equimolar ratio. During the reaction, the temperature was gradually elevated to a final temperature of 180° C. to complete esterification. The reaction product was cooled and washed with water. The catalyst and the chlorine content were removed to obtain a phosphoric ester mixture (designated FR-3). The GPC analysis revealed that FR-3 comprises TPP-OH, bis(resorcinyl)-phenyl phosphate of formula (e) shown below (hereinafter referred to as TPP-(OH)$_2$), a hydroxyl-containing aromatic condensed phosphoric ester of formula (f) shown below (hereinafter referred to as TPP dimer-OH), TPP, TPP dimer, and TPP oligomer at a ratio of 3.2/5.8/25.3/2.1/34.7/28.9.

TPP—(OH)$_2$:

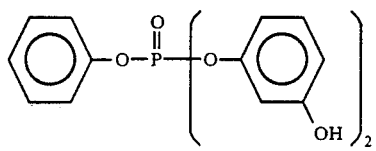

(e)

TPP Dimer-OH:

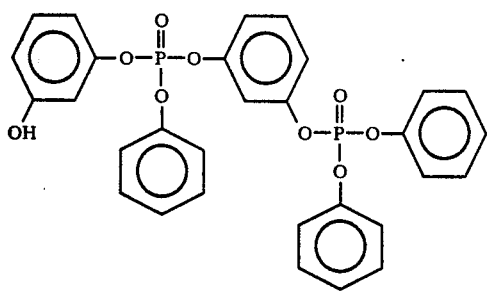

2-4) Aromatic Condensed Phosphoric Ester (FR-4)

A commercially available aromatic condensed phosphoric ester, "CR 733S" produced by Daihachi Chemical Industry Co., Ltd., (hereinafter referred to as FR-4) was used.

The GPC analysis revealed that FR-4 comprises TPP dimer and TPP oligomer at a ratio of 65/35.

2-5) Hydroxyphenyl-Containing Organophosphorus Compound (FR-5)

FR-5 was prepared in the same manner as for FR-1, except for using 141.0 parts (molar ratio: 2.0) of cresol in place of 122.7 parts (molar ratio: 2.0) of phenol.

The GPC analysis revealed that FR-5 comprises dicresyl resorcinyl phosphate of formula (g) shown below (hereinafter referred to as TCP-OH), tricresyl phosphate (hereinafter abbreviated as TCP), an aromatic condensed phosphoric ester of formula (h), wherein n=1, shown below (hereinafter referred to as TCP dimer), and an aromatic condensed phosphoric ester of formula (h), wherein n≧2, (hereinafter referred to as TCP oligomer) at a ratio of 54.5/11.2/31.2/3.1.

TCP—OH:

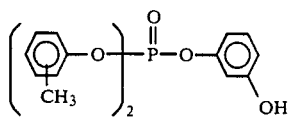

TCP Dimer and TCP Oligomer:

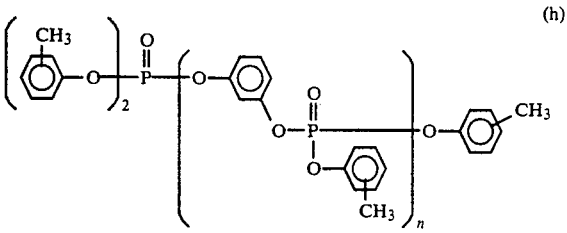

n = 1 TCP dimer
n ≧ 2 TCP oligomer

2-6) Hydroxyphenyl-Containing Organophosphorus Compound (FR-6)

In the preparation of FR-3, the intermediate product (C) was isolated and purified. The product (hereinafter referred to as FR-6) was found by GPC analysis to comprise TPP-(OH)$_2$, TPP dimer, and TPP oligomer at a ratio of 44.1/35.3/20.6.

2-7) Organophosphorus Compound Containing No Hydroxyphenyl Group (TPP)

Commercially available triphenyl phosphate (TPP) produced by Daihachi Chemical Industry Co., Ltd., was used.

3) FLAME-RETARDANT

3-1) Red Phosphorus (RP-1)

Commercially available red phosphorus powder, "Novaexcel 150" produced by Rinkagaku Kogyo Co., Ltd., (hereinafter referred to as RP-1) was used.

3-2) Electroless Plating-Stabilized Red Phosphorus (RP-2)

In a 3 l beaker was put 1 l of a 0.1 g/l solution of palladium trichloride in a 1N hydrochloric acid aqueous solution, and 100 g of industrial red phosphorus having an average particle size of 20 μm was added thereto and reacted at room temperature for 10 minutes. The reaction product was collected by filtration and dried.

The thus obtained palladium chloride-treated red phosphorus was suspended in 1 l of a 20 g/l aqueous solution of ammonium chloride as a complexing agent by stirring in a beaker, and the suspension was heated to 60° C. To the suspension were separately fed 41 ml of a 224 g/l nickel sulfate solution and 41 ml of a mixed solution of 226 g/l of sodium hypophosphite and 128 g/l of sodium hydroxide, and the mixture was allowed to react for 30 minutes.

The resulting stabilized red phosphorus (hereinafter referred to as RP-2) was observed under an optical microscope. The red phosphorus particles were found to be completely and uniformly coated with a film with a metallic luster. 98% of the nickel charged was consumed.

3-3) Non-Stabilized Red Phosphorus (RP-3)

Commercially available red phosphorus produced by Nippon Chemical Industrial Co., Ltd. was used without stabilization (hereinafter referred to as RP-3).

3-4) Thermoplastic Resin-Encapsulated Electroless Plated Red Phosphorus (RP-4)

In 400 ml of dimethylformamide was dissolved 100 g of a polystyrene resin, "Asahi Kasei Polystyrene 685" produced by Asahi Chemical Industry Co., ltd. To the solution were added 150 g of the stabilized red phosphorus (RP-2) obtained in (3-2) above and 110 g of magnesium hydroxide having an average particle size of 5 μm, followed by stirring.

The mixture was poured into a cup having an inner diameter of 5 cm and 20 holes having a diameter of 4 mm on the same plane on the periphery thereof which was connected to a motor via a bearing and was rotating at 800 rpm. The liquid drops thus formed were brought into contact with a cylindrical water curtain at the radius of 25 cm from the axis of the rotating cup to precipitate the resin. The resulting granules were washed to remove the solvent and dried to obtain spherical red phosphorus capsules having an average particle size of 0.8 mm (hereinafter referred to as RP-4). RP-4 had a void volume of 64% and a red phosphorus content of 38%.

3-5) Triazine Skeleton-Containing Compound (ML)

Commercially available melamine produced by Mitsui Toatsu Chemicals, Inc. (hereinafter abbreviated as ML) was used.

3-6) Triazine Skeleton-Containing Compound (MC)

Commercially available melamine cyanurate, "MC 610" produced by Nissan Chemical Industries, Ltd., (hereinafter referred to as MC) was used.

4) HIGHER FATTY ACID AMIDE

Commercially available ethylene-bis-stearamide, "Kao Wax EB FF" produced by Kao Co., Ltd., (hereinafter referred to as EBS) was used.

EXAMPLES 1 TO 5 AND COMPARATIVE EXAMPLES 1 TO 6

The components shown in Table 1 below were mechanically mixed at the compounding ratio shown, and the mixture was melted in Laboplastomill manufactured by Toyo Seiki Seisakusho at 250° C. and 50 rpm for 5 minutes. The resulting resin composition was heat-pressed to prepare ⅛ inch-thick specimens, and evaluation was made with respect to Vicat softening temperature, Izod impact strength, and MFR. The results obtained are shown in FIG. 1 and Table 1.

TABLE 1

| Example No. | Thermoplastic Resin | | Flow Modifier | | | | | MFR (g/10 min) | Izod Impact Strength (kg · cm/cm) | Vicat Softening Temp. (°C.) |
|---|---|---|---|---|---|---|---|---|---|---|
| | HIPS-1 | PPE-MB | TPP-OH | TPP | TPP Dimer | TPP Oligomer | Total | | | |
| Example 1 | 67 | 33 | 14.6 | 5.0 | 7.4 | 0 | 27 (FR-1) | 10.3 | 14.2 | 98.8 |
| Example 2 | 67 | 33 | 12.5 | 4.2 | 6.3 | 0 | 23 (FR-1) | 8.4 | 13.6 | 98.5 |
| Example 3 | 67 | 33 | 10.3 | 3.5 | 5.2 | 0 | 19 (FR-1) | 5.1 | 13.6 | 99.0 |
| Example 4 | 67 | 33 | 8.1 | 2.8 | 4.1 | 0 | 15 (FR-1) | 4.2 | 13.6 | 99.8 |
| Example 5 | 67 | 33 | 4.3 | 1.5 | 2.2 | 0 | 8 (FR-1) | 1.6 | 13.5 | 105.9 |
| Compara. Example 1 | 67 | 33 | 0 | 0 | 0 | 0 | 0 | 0.3 | 14.9 | 123.8 |
| Compara. Example 2 | 67 | 33 | 0 | 27 | 0 | 0 | 27 (TPP) | 24.4 | 12.7 | 66.5 |
| Compara. Example 3 | 67 | 33 | 0 | 23 | 0 | 0 | 23 (TPP) | 16.3 | 12.6 | 72.8 |
| Compara. Example 4 | 67 | 33 | 0 | 19 | 0 | 0 | 19 (TPP) | 10.2 | 11.5 | 79.8 |
| Compara. Example 5 | 67 | 33 | 0 | 15 | 0 | 0 | 15 (TPP) | 5.9 | 11.5 | 86.9 |
| Compara. Example 6 | 67 | 33 | 0 | 8 | 0 | 0 | 8 (TPP) | 1.8 | 11.5 | 102.6 |

It can be seen from FIG. 1 and Table 1 that the organophosphorus compound containing a hydroxyphenyl group endows thermoplastic resins with improved flow while retaining impact resistance and heat resistance.

EXAMPLES 6 TO 8

A resin composition was prepared from the components shown in Table 2 below and evaluated in the same manner as in Example 1. The results obtained are shown in Table 2.

TABLE 2

| Example No. | Thermoplastic Resin | | Flow Modifier | | | | | | | | MFR (g/10 min) | Izod Impact Strength (kg · cm/cm) | Vicat Softening Temp. (°C.) |
|---|---|---|---|---|---|---|---|---|---|---|---|---|---|
| | HIPS-1 | PPE-MB | TPP-OH | TPP-OH-P | TPP-(OH)₂ | TPP Dimer-OH | TPP | TPP Dimer | TPP Oligomer | Total | | | |
| Example 3 | 67 | 33 | 10.3 | 0 | 0 | 0 | 3.5 | 5.2 | 0 | 19 (FR-1) | 5.1 | 13.6 | 99.0 |
| Example 6 | 67 | 33 | 0 | 12.3 | 0 | 0 | 2.4 | 3.2 | 1.1 | 19 (FR-2) | 5.0 | 13.2 | 102.2 |
| Example 5 | 67 | 33 | 4.3 | 0 | 0 | 0 | 1.5 | 2.2 | 0 | 8 (FR-1) | 1.6 | 13.5 | 105.9 |
| Example 7 | 67 | 33 | 0 | 5.2 | 0 | 0 | 1.0 | 1.3 | 0.5 | 8 (FR-2) | 1.5 | 12.8 | 108.8 |
| Example 8 | 67 | 33 | 0.6 | 0 | 1.1 | 4.8 | 0.4 | 6.6 | 5.5 | 19 (FR-3) | 4.0 | 15.5 | 110.4 |

EXAMPLES 9 TO 11 AND COMPARATIVE EXAMPLES 7 TO 10

A resin composition was prepared from the components shown in Table 3 below in the same manner as in Example 1, except that the resin melting temperature was changed to 230° C. The resin composition was evaluated in the same manner as in Example 1. The results obtained are shown in FIG. 2 and Table 3.

Figure 2:
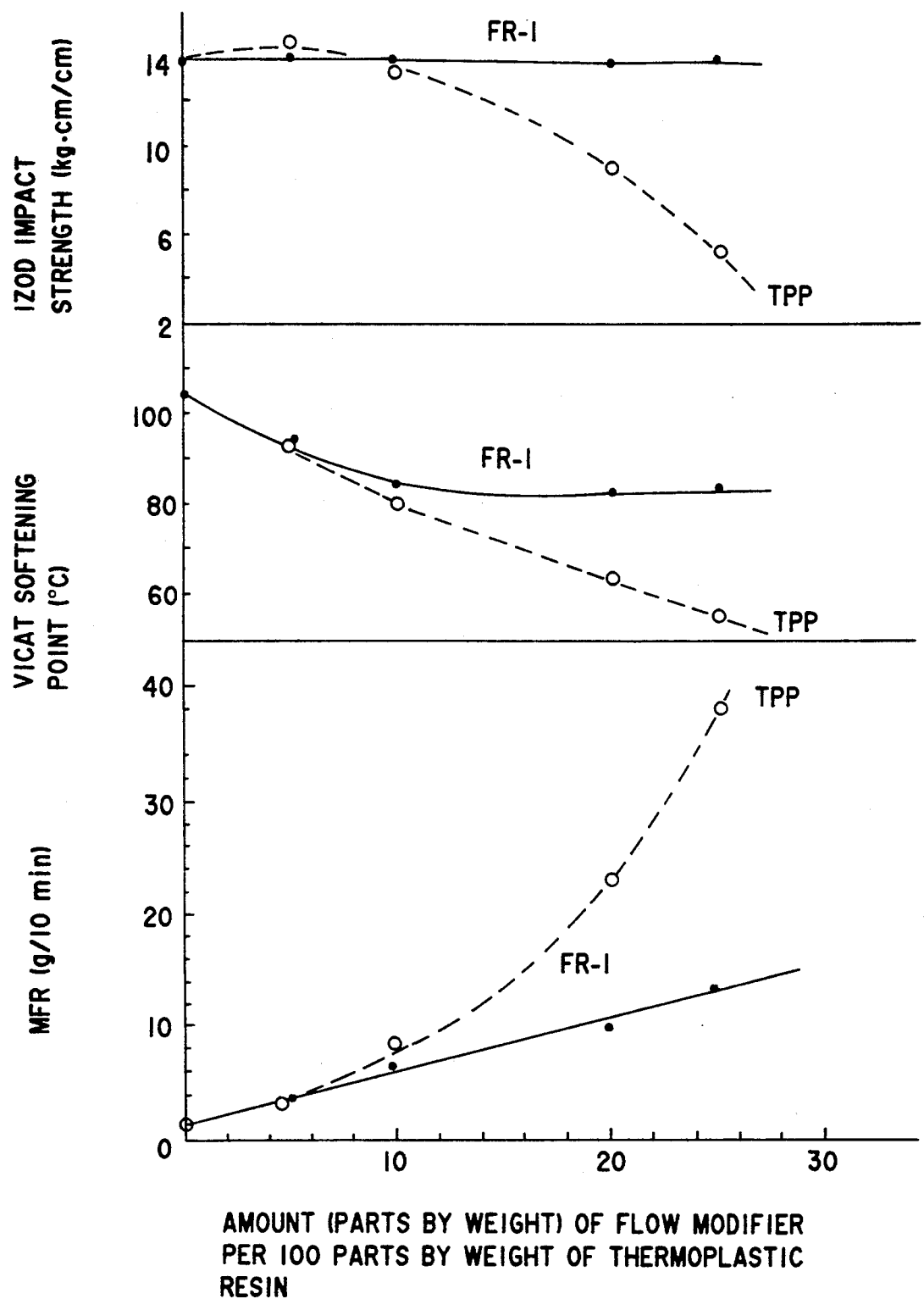
FIG. 2 is a graph showing the relationship of the amount (parts by weight) of a hydroxyphenyl-containing organophosphorus compound (FR-1) or an organophosphorus compound containing no hydroxyphenyl group (TPP) per 100 parts by weight of a thermoplastic resin used in Examples 9 to 11 and Comparative Examples 7 to 10 to Izod impact strength, Vicat softening point, or melt flow rate (MFR) of a resin composition containing the same.

It can be seen from FIG. 2 and Table 3 that the hydroxyphenyl-containing organophosphorus compound improves flow while retaining impact resistance and heat resistance.

TABLE 3

| Example No. | Thermoplastic Resin HIPS-2 | Flow Modifier | | | | | MFR (g/10 min) | Izod Impact Strength (kg · cm/cm) | Vicat Softening Temp. (°C.) |
|---|---|---|---|---|---|---|---|---|---|
| | | TPP-OH | TPP | TPP Dimer | TPP Oligomer | Total | | | |
| Example 9 | 100 | 13.5 | 4.6 | 6.9 | 0 | 25 (FR-1) | 13.2 | 13.8 | 83.7 |
| Example 10 | 100 | 10.8 | 3.7 | 5.5 | 0 | 20 (FR-1) | 9.9 | 13.8 | 83.8 |
| Example 11 | 100 | 5.4 | 1.8 | 2.8 | 0 | 10 (FR-1) | 6.3 | 13.9 | 84.3 |
| Compara. Example 7 | 100 | 0 | 0 | 0 | 0 | 0 | 1.3 | 13.8 | 105.6 |
| Compara. Example 8 | 100 | 0 | 25 | 0 | 0 | 25 (TPP) | 38.0 | 5.2 | 55.4 |
| Compara. Example 9 | 100 | 0 | 20 | 0 | 0 | 20 (TPP) | 23.0 | 8.9 | 64.2 |
| Compara. Example 10 | 100 | 0 | 10 | 0 | 0 | 10 (TPP) | 8.5 | 13.5 | 80.1 |

EXAMPLES 12 AND 13 AND COMPARATIVE EXAMPLES 11 TO 14

A resin composition was prepared from the components shown in Table 4 below and evaluated in the same manner as in Example 1. The results obtained are shown in Table 4.

As is apparent from Table 4, various thermoplastic resins containing the hydroxyphenyl-containing organophosphorus compound, e.g., TPP-OH, provide a composition having excellent and well-balanced physical properties. To the contrary, the resin compositions using the organophosphorus compound containing no hydroxyl group, e.g., TPP, exhibit improved flow but poor heat resistance.

Figure 3:
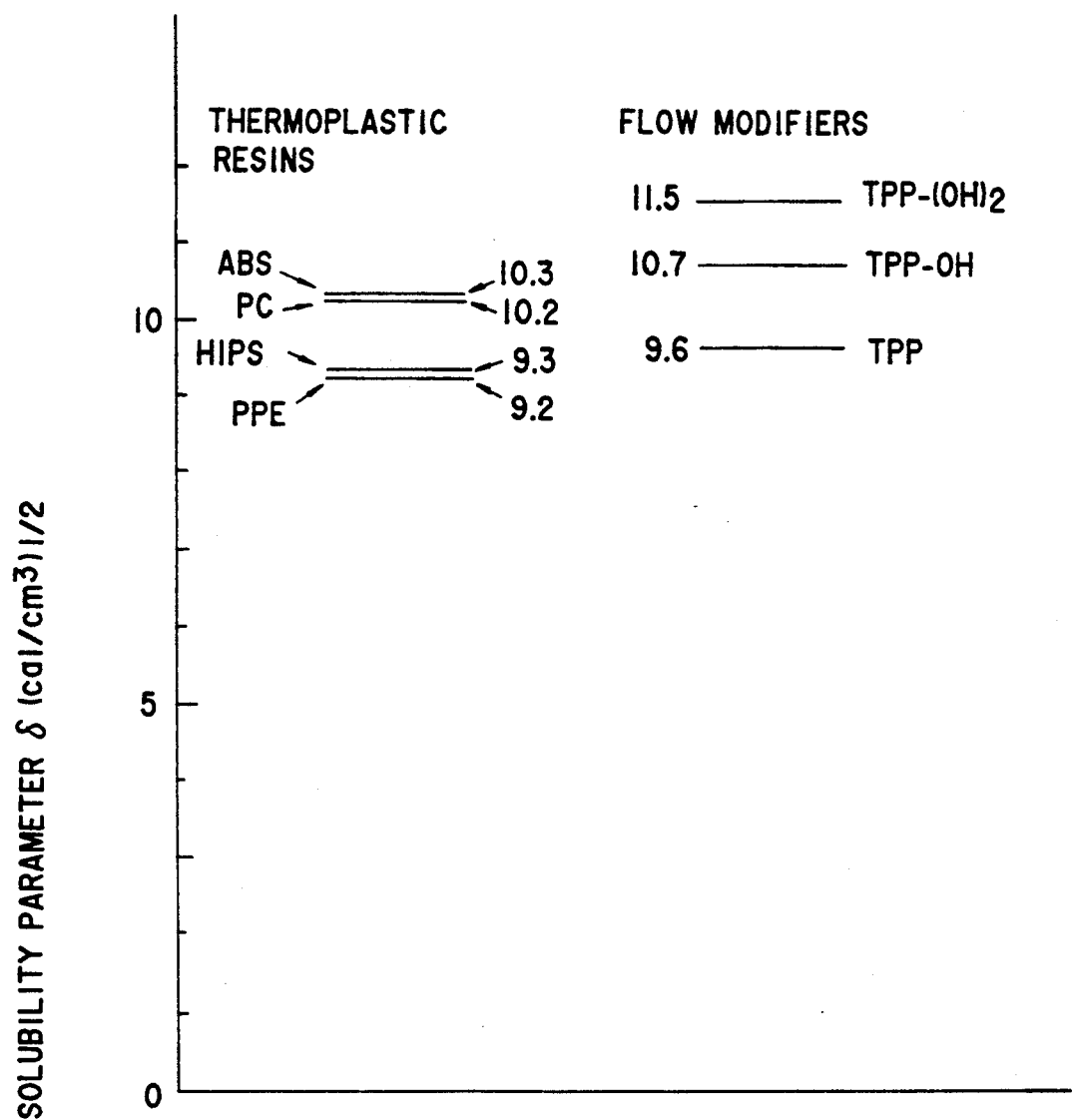
FIG. 3 is a graph showing the solubility parameter of thermoplastic resins and flow modifiers.

Polarity, i.e., an SP value will account for the above difference of the results. FIG. 3 shows a diagram of SP values of thermoplastic resins and flow modifiers. SP values ($\delta$) can be obtained from the Small-Hoy formula shown below as described in *Polymer Handbook*, IV-339, John Wiley & Sons, New York.

$$\delta = d\Sigma G/M$$

wherein $\Sigma G$ represents the sum of the group molar attraction constants of atoms or molecules; d represents a density; and M represents a molecular weight.

As shown in FIG. 3, the SP value of HIPS or PPE is very close to that of TPP but is slightly different from that of TPP-OH. In other words, HIPS and/or PPE exhibit complete compatibility with TPP and partial compatibility with TPP-OH. Therefore, the resin composition comprising HIPS or HIPS/PPE and the flow modifier containing TPP-OH exhibits excellent physical properties in good balance. As compared with HIPS or PPE, on the other hand, ABS (acrylonitrile/-butadiene/styrene: 26/14/60) or PC has a SP value slightly closer to that of TPP-OH and has so increased compatibility with TPP-OH. As a result, the effect of TPP-OH in improving heat resistance exerted on ABS or PC is weaker than on HIPS or PPE.

TABLE 4

| Example No. | Thermo-Plastic Resin HIPS-2 | Flow Modifier | | | | | MFR (g/10 min) | Izod Impact Strength (kg · cm/cm) | Vicat Softening Temp. (°C.) |
|---|---|---|---|---|---|---|---|---|---|
| | | TPP-OH | TPP | TPP Dimer | TPP Oligomer | Total | | | |
| Compara. Example 1 | HIPS-1/ PPE-MB (67/33) | 0 | 0 | 0 | 0 | 0 | 0.3 | 14.9 | 123.8 |
| Example 1 | HIPS-1/ PPE-MB (67/33) | 14.6 | 5.0 | 7.4 | 0 | 27 (FR-1) | 10.3 | 14.2 | 98.8 |
| Compara. Example 2 | HIPS-1/ PPE-MB (67/33) | 0 | 27 | 0 | 0 | 27 (TPP) | 24.4 | 12.7 | 66.5 |
| Compara. Example 7 | HIPS-2 (100) | 0 | 0 | 0 | 0 | 0 | 1.3 | 13.8 | 105.6 |
| Example 8 | HIPS-2 (100) | 13.5 | 4.6 | 6.9 | 0 | 25 (FR-1) | 13.2 | 13.8 | 83.7 |
| Compara. Example 8 | HIPS-2 (100) | 0 | 25 | 0 | 0 | 25 (TPP) | 38.0 | 5.2 | 55.4 |
| Compara. Example 11 | ABS (100) | 0 | 0 | 0 | 0 | 0 | 1.6 | 15.5 | 105.7 |
| Example 12 | ABS (100) | 13.5 | 4.6 | 6.9 | 0 | 25 (FR-1) | 25.3 | 5.0 | 68.5 |
| Compara. Example 12 | ABS (100) | 0 | 25 | 0 | 0 | 25 (TPP) | 41.5 | 5.1 | 64.9 |
| Compara. Example 13 | PC (100) | 0 | 0 | 0 | 0 | 0 | 0.12 | 8.8 | 154.2 |
| Example 13 | PC (100) | 13.5 | 4.6 | 6.9 | 0 | 25 (FR-1) | 11.4 | 2.6 | 85.4 |
| Compara. | PC (100) | 0 | 25 | 0 | 0 | 25 | 17.1 | 2.8 | 78.5 |

TABLE 4-continued

| Example No. | Resin Composition (weight ratio) | | | | | MFR (g/10 min) | Izod Impact Strength (kg·cm/cm) | Vicat Softening Temp. (°C.) |
|---|---|---|---|---|---|---|---|---|
| | Thermo-Plastic Resin HIPS-2 | Flow Modifier | | | | | | |
| | | TPP-OH | TPP | TPP Dimer | TPP Oligomer | Total | | |
| Example 14 | | | | | | (TPP) | | |

EXAMPLES 14 AND 15 AND COMPARATIVE EXAMPLES 15 AND 16

A resin composition was prepared from the components shown in Table 5 below and evaluated in the same manner as in Example 1. Evaluation of flame retardance was additionally made. The results obtained are shown in Table 5.

The results in Table 5 prove that the hydroxyphenyl-containing organophosphorus compound provides resin compositions excellent in balance of flame retardance, flow, heat resistance, and impact resistance.

EXAMPLES 16 TO 18

A resin composition was prepared from the components shown in Table 6 below and evaluated in the same manner as in Example 14. The results obtained are shown in Table 6.

TABLE 6

| Example No. | Resin Composition (weight ratio) | | | | | Burning Test | | | MFR (g/10 min) | Izod Impact Strength (kg cm/cm) | Vicat Softening Temp. (°C.) |
|---|---|---|---|---|---|---|---|---|---|---|---|
| | Thermoplastic Resin | Flow Modifier | Flame-Retardant | | | Flame-out Time (sec) | Drip-ping | Judg-ment | | | |
| | | | RP-1 | MC | EBS | | | | | | |
| Example 16 | HIPS-1/PPE/MB (67/33) | 19 (FR-1) | 0 | 15 | 2 | 4.0 | none | V-0 | 6.9 | 7.2 | 96.3 |
| Example 17 | HIPS-1/PPE/MB (67/33) | 19 (FR-2) | 0 | 15 | 2 | 3.5 | none | V-0 | 7.2 | 7.3 | 100.7 |
| Example 18 | HIPS-1/PPE/MB (67/33) | 19 (FR-5) | 0 | 15 | 2 | 5.0 | none | V-0 | 6.2 | 6.6 | 95.0 |

EXAMPLE 19 AND COMPARATIVE EXAMPLES 17 AND 18

A resin composition was prepared from the components shown in Table 7 below and evaluated in the same manner as in Example 14. The results obtained are shown in Table 7.

TABLE 5

| Example No. | Resin Composition (weight ratio) | | | | | | | |
|---|---|---|---|---|---|---|---|---|
| | Thermoplastic Resin | Flow Modifier | | | | | Flame-Retardant | |
| | | TPP—OH | TPP | TPP Dimer | Oligomer | Total | RP-1 | ML |
| Example 14 | HIPS-1/PPE-MB (76/24) | 11.4 | 3.8 | 5.8 | 0 | 21 (FR-1) | 2 | 13 |
| Compara. Example 15 | HIPS-1/PPE-MB (76/24) | 0 | 21 | 0 | 0 | 21 (TPP) | 2 | 13 |
| Compara. Example 16 | HIPS-1/PPE-MB (76/24) | 0 | 0 | 13.7 | 7.3 | 21 (FR-4) | 2 | 13 |
| Example 15 | HIPS-1/PPE-MB (76/24) | 6.8 | 2.3 | 9.0 | 2.9 | 21 (FR-1/FR-4 12.6/8.4) | 2 | 13 |

| Example No. | Burning Test | | | MFR (g/10 min) | Izod Impact Strength (kg cm/cm) | Vicat Softening Temp. (°C.) |
|---|---|---|---|---|---|---|
| | Flame-out Time (sec) | Drip-ping | Judg-ment | | | |
| Example 14 | 2.4 | none | V-0 | 15.1 | 7.1 | 93.7 |
| Compara. Example 15 | 2.2 | none | V-0 | 19.0 | 4.8 | 75.1 |
| Compara. Example 16 | 2.5 | none | V-0 | 12.5 | 3.9 | 88.6 |
| Example 15 | 2.3 | none | V-0 | 13.9 | 6.1 | 91.2 |

As is apparent from Table 7 in view of FIG. 3, since the hydroxyphenyl-containing organophosphorus compound containing two hydroxyl groups per molecule has an SP value fairly far from that of the resin component (HIPS or PPE), the resin composition undergoes phase separation to exhibit a deteriorated balance of physical properties.

deposit. The thermoplastic resin composition further containing a flame-retardant exhibits excellent flowability and flame retardance as well as heat resistance and impact resistance. The resin composition of the present invention is suitable as a molding material for parts of appliances, parts of OA equipment, etc., making it possible particularly by virtue of its easy flow not only to produce large-sized and thin-walled molded articles but to set the molding condition at a relatively low temperature to thereby reduce the molding cycle. These effects are deemed great contribution to the industrial field.

While the invention has been described in detail and with reference to specific examples thereof, it will be apparent to one skilled in the art that various changes and modifications can be made therein without departing from the spirit and scope thereof.

What is claimed is:

1. A flow modifier for a thermoplastic resin comprising a hydroxyphenyl-containing organophosphorus compound represented by formula (I):

TABLE 7

| Example No. | Resin Composition (weight ratio) | | | | | Burning Test | | | MFR (g/10 min) | Izod Impact Strength (kg cm/cm) | Vicat Softening Temp. (°C.) | Compatibility |
|---|---|---|---|---|---|---|---|---|---|---|---|---|
| | Thermoplastic Resin | Flow Modifier | | ML | EBS | Flowout Time (sec) | Dripping | Judgment | | | | |
| | | Kind and Amount | Number of OH Groups | | | | | | | | | |
| Compara. Example 17 | HIPS-3/PPE-MB (71/29) | 20 (TPP) | 0 | 16 | 2 | 4.0 | none | V-0 | 10.4 | 5.3 | 76.0 | satisfactory |
| Example 19 | HIPS-3/PPE-MB (71/29) | 20 (FR-1) | 1 | 16 | 2 | 4.0 | none | V-0 | 8.1 | 10.1 | 97.0 | satisfactory |
| Compara. Example 18 | HIPS-3/PPE-MB (71/29) | 20 (FR-6) | 2 | 16 | 2 | 28.0 | observed | HB* | 1.7 | 7.0 | 116.0 | phase separation |

Note: HB* Any of the ranks UL-94, V-0, V-1, and V-2 was reached.

EXAMPLES 20 TO 28

A resin composition was prepared from the components shown in Table 8 below and evaluated in the same manner as in Example 14. The amount of phosphine generated during extrusion and the burning test was also measured. The results obtained are shown in Table 8.

TABLE 8

| Example No. | Resin Composition (weight ratio) | | | | Burning Test | Phosphine (Extrusion/Burning) |
|---|---|---|---|---|---|---|
| | Thermoplastic Resin | Flow Modifier | Flame-Retardant | | | |
| | | | Kind | Amount (ppm) | | |
| Example 20 | HIPS-2/PPE (80/20) | FR-1 (20) | RP-2 | 15 | V-0 | 0/0 |
| Example 21 | HIPS-2/PPE (80/20) | FR-1 (20) | " | 10 | V-0 | 0/0 |
| Example 22 | HIPS-2/PPE (80/20) | FR-1 (20) | " | 5 | V-0 | 0/0 |
| Example 23 | HIPS-2/PPE (80/20) | FR-1 (20) | " | 2 | V-0 | 0/0 |
| Example 24 | HIPS-2/PPE (80/20) | FR-1 (20) | RP-3 | 5 | V-0 | 0/0 |
| Example 25 | HIPS-2/PPE (80/20) | FR-1 (20) | RP-4 | 15 | V-0 | 0/0 |
| Example 26 | HIPS-2/PPE (80/20) | FR-1 (20) | " | 10 | V-0 | 0/0 |
| Example 27 | HIPS-2/PPE (80/20) | FR-1 (20) | " | 5 | V-0 | 0/0 |
| Example 28 | HIPS-2/PPE (80/20) | FR-1 (20) | " | 2 | V-0 | 0/0 |

The flow modifier according to the present invention, when compounded with a thermoplastic resin, provides a thermoplastic resin composition having improved flowability without causing a reduction in impact resistance, a reduction in heat resistance, or a mold

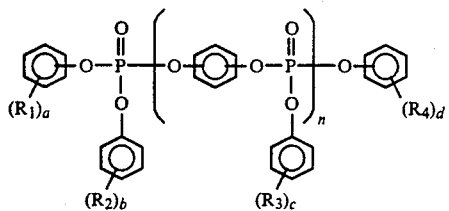

wherein $R_1$, $R_2$, $R_3$, and $R_4$ each represents a hydroxyl group,

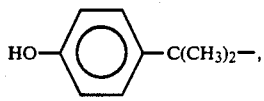

a hydrogen atom, or an alkyl group having 1 to 6 carbon atoms; a, b, c, and d each represents an integer of from 1 to 3; n represents 0 or an integer of from 1 to 3; when n is 0 or 1, the compound contains one hydroxyl group or

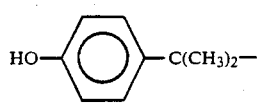

group per molecule; and when n is 2 or 3, the compound contains one or two, in total, of hydroxyl group and

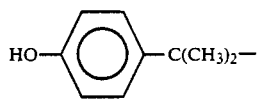

group per molecule.

2. A flow modifier as claimed in claim 1, wherein said hydroxyphenyl-containing organophosphorus compound is a compound represented by formula (III):

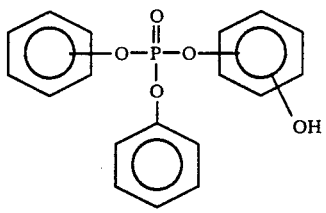

wherein the hydroxyl group is at the meta- or para-position.

3. A thermoplastic resin composition containing (i) a thermoplastic resin and (ii) a flow modifier comprising a hydroxyphenyl-containing organophosphorus compound represented by formula (I):

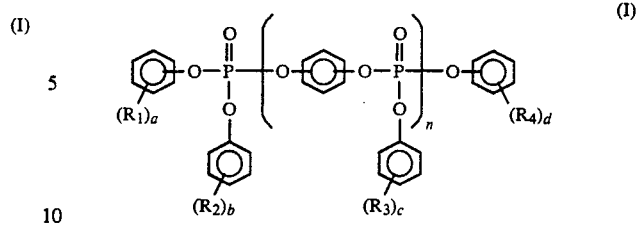

wherein $R_1$, $R_2$, $R_3$, and $R_4$ each represents a hydroxyl group,

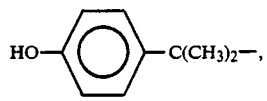

a hydrogen atom, or an alkyl group having 1 to 6 carbon atoms; a, b, c, and d each represents an integer of from 1 to 3; n represents 0 or an integer of from 1 to 3; when n is 0 or 1, the compound contains one hydroxyl group or

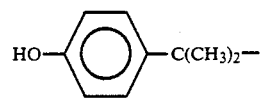

group per molecule; and when n is 2 or 3, the compound contains one or two, in total, of hydroxyl group and

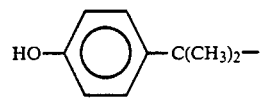

group molecule.

4. A thermoplastic resin composition as claimed in claim 3, wherein said thermoplastic resin is a styrene resin, polyphenylene ether, or polycarbonate.

5. A thermoplastic resin composition as claimed in claim 3, wherein said thermoplastic resin is a polymer blend of a polystyrene resin and polyphenylene ether.

6. A thermoplastic resin composition as claimed in claim 3, wherein said flow modifier is present in an amount of from 5 to 50 parts by weight per 100 parts by weight of the thermoplastic resin.

7. A thermoplastic resin composition as claimed in claim 3, wherein said composition further contains a flame-retardant selected from the group consisting of red phosphorus and a triazine skeleton-containing compound.

8. A thermoplastic resin composition as claimed in claim 7, wherein said thermoplastic resin is a styrene resin, polyphenylene ether, or polycarbonate.

9. A thermoplastic resin as claimed in claim 7, wherein said thermoplastic resin is a polymer blend of a polystyrene resin and polyphenylene ether.

10. A thermoplastic resin composition as claimed in claim 7, wherein said flow modifier is present in an amount of from 5 to 50 parts by weight and said flame-retardant is present in an amount of not more than 30 parts by weight, per 100 parts by weight of the thermoplastic resin.

* * * * *